United States Patent
Jenkins et al.

(10) Patent No.: US 8,318,710 B2
(45) Date of Patent: Nov. 27, 2012

(54) SKIN TREATMENTS

(75) Inventors: Gail Jenkins, Sharnbrook (GB); Andrew Easson Mayes, Sharnbrook (GB)

(73) Assignee: Conopco, Inc., Englewood Cliffs, NJ (US)

( * ) Notice: Subject to any disclaimer, the term of this patent is extended or adjusted under 35 U.S.C. 154(b) by 101 days.

(21) Appl. No.: 12/792,852

(22) Filed: Jun. 3, 2010

(65) Prior Publication Data

US 2010/0240628 A1 Sep. 23, 2010

Related U.S. Application Data

(63) Continuation of application No. 10/557,944, filed on Nov. 21, 2005, now abandoned.

(30) Foreign Application Priority Data

May 22, 2003 (GB) .................................. 0311815.5

(51) Int. Cl.
*A01N 45/00* (2006.01)
*A01N 31/04* (2006.01)

(52) U.S. Cl. ........................................ 514/171; 514/725

(58) Field of Classification Search .................. 514/171, 514/725

See application file for complete search history.

(56) References Cited

U.S. PATENT DOCUMENTS

| 5,587,367 A | 12/1996 | Reichert et al. |
| 5,972,341 A | 10/1999 | Andre et al. |
| 2002/0103139 A1 | 8/2002 | Weisspapir et al. |
| 2002/0110572 A1 * | 8/2002 | Chandar et al. ............... 424/401 |
| 2003/0124159 A1 | 7/2003 | Jenkins et al. |

FOREIGN PATENT DOCUMENTS

| WO | 92/07586 | 5/1992 |
| WO | 98/32444 | 7/1998 |
| WO | 03/030857 A1 | 4/2003 |
| WO | WO 03/030857 | * 4/2003 |

OTHER PUBLICATIONS

Fogh (Expression, Purification, and Binding Properties of Human Cellular Retinois Acid-Binding Protein Type I and Type II, Archives of Biochemistry and Biophysics, vol. 300, No. 2, 1993).*
International Search Report Appln. No. PCT/EP2004/004942-mailed Jan. 31, 2005.
Griffiths et al. "Restoration of Collagen Formation in Photodamaged Human Skin by Tretinoin (Retinoic Acid)" N. Eng. J. Med. (1993) 329, pp. 530-535.
Delva et al. "Physical and Functional Interactions between Cellular Retinoic Acid Binding Protein and the Retinoic Acid-Dependent Nuclear Complex" 1999, Mol, & Cell. Biol. 19, pp. 7158-7167.
Rahman et al., Microbial Transformations of Hypolipemic E-Guggulsterone. J. Nat. Prod. 1998, 61 (4), pp. 426-431.

* cited by examiner

*Primary Examiner* — Benjamin Packard
*Assistant Examiner* — Adam C Milligan
(74) *Attorney, Agent, or Firm* — Michael P. Aronson

(57) ABSTRACT

Compositions comprising an LXR activator and retinoic acid and/or a metabolic precursor thereto are useful in reducing the effects of chronoageing and/or photoageing of the skin.

4 Claims, No Drawings

SKIN TREATMENTS

This is a Continuation of co-pending U.S. patent application Ser. No. 10/557,944, filed Nov. 21, 2005, which is a national stage application under 35 U.S.C. §371 of PCT International Application PCT/EP2004/004942 filed May 6, 2004, which claims priority under 35 U.S.C. §119 to EP Application No. 0311815.5 filed May 22, 2003; all of which are incorporated herein in their entirety, by reference.

FIELD OF THE INVENTION

The invention relates to the field of topical or systemic compositions and more particularly to compositions comprising a combination of retinoic acid and a Liver-X-receptor (LXR) agonist and their use in providing a variety of skin care benefits by slowing or inhibiting photo-induced or age-related skin damage.

BACKGROUND TO THE INVENTION

Skin is subject to deterioration through dermatological disorders, environmental abuse (wind, air conditioning, central heating) or through the normal ageing process (chronoageing) which may be accelerated by exposure of skin to sun (photoageing). In recent years the demand for cosmetic methods for improving the appearance and condition and, in particular, for reversing, reducing or preventing the visible signs of wrinkled, aged and/or photodamaged skin has grown enormously.

Consumers are increasingly seeking "anti-ageing" products that reverse, treat or delay the visible signs of chronoaging and photoaging skin such as wrinkles, lines, sagging, hyperpigmentation and age spots.

It is known in the art that retinoic acid is a potent anti-ageing active and induces dermal repair of photodamaged skin. It has been shown that wrinkle effacement and dermal repair following topical treatment of skin with retinoic acid arises through new collagen deposition and synthesis in the skin (for example, Griffiths et al. N. Eng. J. med. (1993) 329, 530-535). It is widely accepted that strengthening of the dermal matrix by boosting the level of collagen in skin using retinoic acid provides anti-ageing/dermal repair benefits.

The Liver-X-receptor (LXR) is a nuclear receptor known to be present in human keratinocytes where it plays an integral role in the regulation of cell proliferation and differentiation as well as lipid metabolism within the epidermis.

SUMMARY OF THE INVENTION

The present invention is based on a finding that LXR activators enhance the effects of retinoic acid i.e. that LXR activators and retinoic acid act synergistically. In particular, it is shown that LXR activators and retinoic acid act synergistically to upregulate CRAB P II expression in dermal fibroblasts, a well recognised marker of retinoic acid (RA) responsiveness and a transcriptional regulator in RA signalling (Delva et al., 1999, Mol. & Cell Biol. 19, 7158-7167)

Since upregulation of CRAB P II expression is known to correlate with the ability to reverse the physiological changes induced by chronological ageing and/or photoageing, a combination of an LXR activator and retinoic acid, and/or a metabolic precursor thereto, will be effective in the treatment and prevention of normal, but cosmetically undesirable, skin conditions, due to chronoaging or photoaging, such as wrinkles, lines, and sagging may be obtained through the application of cosmetic (topical) or oral compositions to the skin which comprises an LXR activating ligand in combination with retinoic acid and/or a metabolic precursor thereto.

Any reference herein to an activator of LXR includes a reference to an activator of LXRβ and/or of LXRβ, unless specifically stated to the contrary.

Accordingly, in a first aspect of the present invention a composition is provided comprising (i) an LXR activator other than 25-hydroxycholesterol and (ii) retinoic acid and/or a metabolic precursor thereto.

A second aspect of the present invention provides a cosmetic method for reducing chronoageing and/or photoageing of the skin, the method comprising applying to the skin a topical composition comprising (i) an LXR activator other than 25-hydroxycholesterol and (ii) retinoic acid and/or a metabolic precursor thereto.

A third aspect of the present invention comprises a cosmetic method of reducing chronoageing and/or photoageing of the skin, the method comprising dosing topically and/or systemically, an LXR activator and retinoic acid and/or a metabolic precursor thereto. In a preferred embodiment the LXR activator and the retinoic acid and/or metabolic precursor thereto are in the form of a composition.

In one embodiment, the LXR activator and the retinoic acid and/or metabolic precursor thereto are administered by topical application to the skin. In another embodiment, the LXR activator and the retinoic acid and/or metabolic precursor thereto are administered systemically.

The present invention also provides use of a combination of an LXR activator and retinoic acid and/or a metabolic precursor thereto in the manufacture of a composition for topical and/or systemic application for reducing chronoageing and/or photoageing of the skin. Such a composition includes both skin creams, lotions, oils etc (including sunscreen compositions) and personal wash products such as liquid or solid soaps, and bath or shower gels, creams etc.

The present invention further provides a method of enhancing the effect of retinoic acid on skin cells which method comprises administering to the skin cells (i) an LXR activator and (ii) retinoic acid and/or a precursor thereto. Enhancing the effect of retinoic acid on skin cells, such as fibroblasts, includes enhancing expression of retinoic acid responsive genes such as CRAB P II.

DETAILED DESCRIPTION OF THE INVENTION

Unless defined otherwise, all technical and scientific terms used herein have the same meaning as commonly understood by one of ordinary skill in the art.

LXR Activating Agents

Any reference herein to an activator of LXR includes a reference to an activator of LXRα and/or of LXRβ, unless specifically stated to the contrary.

The LXR activating agents can be provided as pure or semi-pure compounds or as crude extracts of natural products, such as plant extracts.

A preferred class of LXR activators comprises the compounds according to the general formulae (A) or (B);

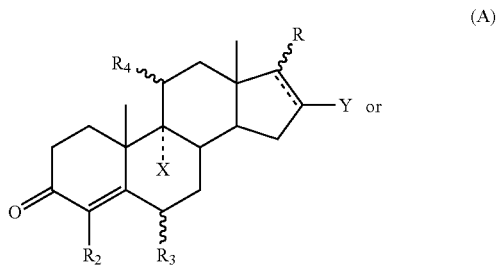

-continued

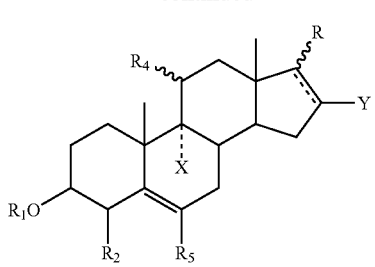

(B)

wherein;

R represents a hydrogen, a hydroxyl, a keto, an acetyl, a $C_1$ to $C_{10}$, substituted or unsubstituted, branched or unbranched, saturated or unsaturated alkyl group;

$R_1$ represents a lower alkyl group, a hydrogen or $COR_6$;

$R_2$ represents a hydrogen, a halogen or a hydroxyl group;

$R_3$ represents a hydrogen, a hydroxyl, a halogen, a keto or a lower alkyl group;

$R_4$ represents a hydrogen, a hydroxyl, or a keto group;

$R_5$ represents a hydrogen, a halogen, a hydroxyl or lower alkyl group;

X represents a hydrogen, a methyl or a halogen;

Y represents a hydrogen, a hydroxyl, a acetyl or a keto group.

One preferred class of LXR activating compound of formula (A) or (B) is that wherein the R represents —H, —OH, =O, —COCH$_3$, —COHCH$_3$, =CHCH$_2$OH, or —OCOCH$_3$.

Another possible class of compounds of formulae (A) and (B) wherein R is $C_1$ to $C_8$ alkyl being substituted or unsubstituted, branched or unbranched and saturated or unsaturated with the proviso that when it is $C_8$, it is unsaturated.

In formulae A and B, the bond by which the R group is linked to the carbon at position 17 will depend on the nature of the R group (indicated by wavy bond). Where R is a hydrogen or a hydroxyl group or acetyl group the bond will be saturated, whereas when R is a keto group the bond will be unsaturated. When R is an alkyl group this group may be linked to the carbon at position 17 via a saturated or unsaturated bond, preferably this is an unsaturated bond.

For the purpose of the present invention R may represent a hydroxyl, a keto or an acetyl group.

R may also represent a $C_1$ to $C_7$ (i.e. including $C_1$, $C_2$, $C_3$, $C_4$, $C_5$, $C_6$ and $C_7$) substituted or unsubstituted, saturated or unsaturated, branched or unbranched alkyl group. Preferably said $C_1$ to $C_7$ alkyl group comprises at least one substituted group selected from hydroxyl, keto and acetyl groups and R may in particular represent substituted alkyl groups having two and three of said substitutions. More preferably the alkyl groups have undergone substitution with one or more keto or hydroxyl groups. Further preferred an alkyl R group is substituted at one or more positions corresponding or equivalent to $C_{20}$, $C_{21}$, $C_{22}$ and $C_{23}$ shown in FIG. 7. Where the substitution is with a keto group this is most preferably bonded to $C_{20}$, whereas when substitution is with a hydroxyl group this is most preferably bonded to a carbon at $C_{21}$ and/or $C_{22}$.

It is preferred that the alkyl R group remains unbranched as this helps to maintain a favoured linear configuration, however in the event that the alkyl group is branch said branches preferably comprise 2 carbons, more preferably 1 carbon.

Where the R group is an alkyl group as described above this will preferably have some degree of unsaturation. Preferably unsaturation occurs in the form of one or more substituted keto groups.

Where R represents an unsaturated $C_1$ to $C_8$ alkyl group it is most preferred that this group has the formula —C(CH$_3$)(CH$_2$)$_2$C=C(CH$_3$)$_2$.

In a preferred embodiment the R group of the LXR activating compound represents a hydrogen, a hydroxyl, a keto or an unsubstituted or, more preferably, substituted $C_1$ to $C_4$ alkyl group. The latter comprise methyl, ethyl, n-propyl, isopropyl, n-butyl, isobutyl or ter-butyl. Preferably substitution occurs at $C_{20}$ or $C_{21}$ within the alkyl group. Where the R group is an alkyl group it is preferred that this is forms an unsaturated bond with $C_{17}$ of the ring structure.

In a most preferred embodiment R is selected from the group consisting of —H, —OH, =O, —COCH$_3$, —COHCH$_3$, =CHCH$_3$, =CHCH$_2$OH, —OCOCH$_3$ and C(CH$_3$)(CH$_2$)$_2$C=C(CH$_3$)$_2$.

A "lower alkyl" as employed herein includes both straight and branched chain radicals of up to four carbon atoms, examples of suitable groups are outlined above. In a preferred embodiment $R_1$ is a hydrogen.

$R_2$ represents a hydrogen, a halogen preferably chlorine or a hydroxyl group, preferably $R_2$ represents a hydrogen.

$R_3$ represents a hydrogen, a halogen preferably a fluorine or chlorine, a keto or a lower alkyl group. Preferably $R_3$ is either a keto group or a hydrogen. In a most preferred embodiment $R_3$ is a hydrogen.

Preferably $R_4$ and $R_5$ represent a hydroxyl group or hydrogen, most preferably these represent a hydrogen.

X preferably represents a hydrogen, a fluorine or a chlorine, most preferably X is a hydrogen.

Preferably Y represents a hydrogen, a hydroxyl or a keto group.

When Y is a hydrogen, in a compound according to general formula A, a double bond may form between $C_{16}$ and $C_{17}$.

In a compound according to formula B, when Y is hydrogen $R_1$ is a preferably hydrogen or —COR$_6$. Preferably when Y is a keto group the activating molecule conforms to general formula A, whereas, when Y is a hydroxyl group the activating molecule preferably conforms to general formula B.

In a most preferred embodiment the activating compound conforms to formula A wherein Y is a keto group.

Where R is a hydrogen or a hydroxyl group, Y is preferably a keto group in an activating compound according to formula A.

Where R is —COCH$_3$, Y is preferably a hydrogen or a keto group in a activating compound according to either A or B, preferably according to formula A.

Where R is =CHCH$_3$ or —OCOCH$_3$, Y is most preferably a keto group in an activating compound according to general formula A.

Where R is =CHCH$_2$OH, Y is preferably either; a hydrogen in an activating compound according to general formula A, wherein $R_4$ is preferably a hydroxyl group; or a hydroxyl group in an activating compound according to formula B wherein $R_1$ is a hydrogen.

Where R is C(CH$_3$)(CH$_2$)$_2$C=C(CH$_3$)$_2$, Y is preferably a hydrogen in an activating compound according to formula B wherein $R_1$ is also a hydrogen.

Some preferred LXR activators are selected from 4-androsten-3,16-dione, 4-androsten-3,16-dione, androst-4-ene-3,6,16-trione, 4-androsten-17beta-ol-3,16-dione acetate, 16-ketotestosterone, 3β-acetoxypregna-5,16-dien-20-one, 3β-acetoxypregna-5-en-20-one, 3β-hydroxypregna-5,16-dien-20-one, 3β-hydroxypregna-5-en-20-one, 5,16-dienpregnane-3,20-diol, 4,16-dienpregna-3,20-dione, 4,17(20)-(cis)-pregnadien-3,16-dione, 4,17(20)-(trans)-pregnadien-3,16-dione, 4-pregnen-3,16,20-trione, 4,17(20)-pregnadien-11beta,21-diol-3-one, 5,17(20)-pregnadien-3,16-dioldiacetate, 5,17(20)-pregnadien-3,16-diol, 5-pregnen-3beta, 16alpha,21-triol-20-one, 24-hydroxychol-4-en-3-one, cholesta-5,24-dien-3β-ol, cis-guggal sterone and desmosterol, and mixtures thereof.

In an especially preferred embodiment, the LXR activator is 4,17(20)-(cis)-pregnadien-3,16-dione.

The preparation of compounds of formulae (A) and (B) has been described in the literature and/or are commercially available e.g. from Sigma Chemical Company.

It is also possible to provide the LXR activator(s) in the form of one or more extracts of natural plant sources, e.g extracts of one or more of *Commiphora mokul, Boswelta serrata*, Dragon's blood resin (*Daemorgos draco*), apple peel, auspice, clove, Damar gum (exudate of Damar tree, Nettle (*Lamium albim*), red seaweed, Breuzihno resin, mastic gum, mountain ash berry and plantain.

A plant extract differs from the intact plant material in that the various components present in the intact plant material will be present in different amounts in the extract, or substantially absent. Prior to extraction, plant materials may be dried and or mechanically processed, e.g. crushed.

Extracts of plant materials are typically made by solvent extraction. Suitable solvents are those in which LXR activators are soluble. Since LXR activators are typically sterols/steroids, suitable solvents include organic solvents such as hexane, chloroform, benzene, petroleum ether, dichloromethane, acetone, ether, diethyl ether, ethyl acetate and mixtures of the above. Solvents may also include alcohols such as methanol, ethanol and isopropyl alcohol and mixtures thereof, optionally mixtures with water. Preferred solvents are those which are acceptable for use in products destined for human or animal use. Plant materials can also be extracted with supercritical liquid $CO_2$ Extraction methods include batch extraction and soxhlet extraction at temperatures up to the solvent boiling point. Extraction procedures may therefore include a heating step. Solvent extracted components may be subject to further purification/separation steps such as chromatography or fractional distillation. As used herein, "fraction" means any fractioned part of a solvent containing one or more of the active ingredients described above, e.g. obtained by chromatography or by fractional distillation.

Sterols/steroids represent the unsaponifiable fractions (unsaps) of seed oils and extracts. These are components that cannot be converted to soaps (e.g. non fatty acid/glyceride material). In some extracts e.g. from oils, the unsaps can be enriched by a process of saponification. A suitable method is as follows:

The lipid extract (~1 g) from e.g. hexane and methanol extractions is refluxed with 2M potassium hydroxide in ethanol for 1 hour. After cooling the mixture is shaken with diethyl ether. The upper solvent layer containing the unsaponifiable fraction is removed and washed twice with water, dried by passing through a column of sodium sulphate and the solvent removed by evaporation under nitrogen at −70° C. This represents the unsaponifiable material (e.g. sterols).

Preferably the composition according to the first aspect of the present invention comprises at least one LXR activator other than a sterol, in particular at least one LXR activator other than any sterol disclosed in U.S. Pat. No. 5,587,367.

Preferably 25-hydroxycholesterol is specifically excluded.

Preferably, dehydroepiandrosterone and its derivatives are specifically excluded.

Retinoic Acid and its Metabolic Precursors

Compositions of the present invention contain retinoic acid and/or one of its metabolic precursors. Many retinoic acid metabolic precursors are commonly known as retinoids. A non-limiting list of such precursors includes those disclosed in U.S. Pat. No. 5,587,367. Examples of the latter include all trans or 13-cis retinoic acid, vitamin A or retinol, as well as its esters such as the acetate, propionate or palmitate of retinol and the aldehyde of vitamin A or retinal.

Some preferred retinoids are selected from retinyl esters, retinol, retinal and retinoic acid, preferably retinol or retinyl ester and mixtures thereof. The term "retinol" includes the following isomers of retinol: all-trans-retinol, 13-cis-retinol, 11-cis-retinol, 9-cis-retinol, 3,4-didehydro-retinol, 3,4-didehydro-13-cis-retinol; 3,4-didehydro-11-cis-retinol; 3,4-didehydro-9-cis-retinol and mixtures thereof. Preferred isomers are all-trans-retinol, 13-cis-retinol, 3,4-didehydro-retinol, 9-cis-retinol. Most preferred is all-trans-retinol, due to its wide commercial availability.

Retinyl ester is an ester of retinol. The term "retinal" has been defined above. Retinyl esters suitable for use in the present invention are $C_1$-$C_{30}$ esters of retinol, preferably $C_2$-$C_{20}$ esters, and most preferably $C_2$, $C_3$, and $C_{16}$ esters because they are more commonly available. Examples of retinyl esters include but are not limited to: retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecandate, retinyl laurate, retinyl tridecanoate, retinyl myristate, retinyl pentadecanoate, retinyl heptadeconoate, retinyl stearate, retinyl isostearate, retinyl nonadecanoate, retinyl arachidonate, retinyl behenate, retinyl linoleate, retinyl oleate.

Preferred esters for use in the present invention are selected from retinyl palmitate, retinyl acetate and retinyl propionate and mixtures thereof, because these are the most commercially available and therefore the cheapest. Retinyl linoleate and retinyl oleate are also preferred due to their efficacy.

Formulations

In a composition according to the invention, the amount of LXR activator, or mixtures thereof, is preferably from 0.00001 wt % to 50 wt %, such as from 0.001 to 35 wt %, more preferably from 0.01% to 10%, most preferably from 0.01 wt % to 1 wt %. The amount of retinoic acid and/or metabolic precursor is preferably from 0.00001% to 50%, such as from 0.001 to 35 wt %, more preferably from 0.001% to 10%, still more preferably from 0.01% to 1%, most preferably from 0.01% to 0.5% by weight.

Preferably, at least one LXR activator and the retinoic acid or metabolic precursor thereof are obtained from different sources.

The composition is typically formulated for topical application or systemic application.

A topical composition for reducing chronoageing and/or photoageing of the skin preferably comprises the LXR activator, the retinoic acid and/or metabolic precursor and a dermatologically acceptable vehicle.

A systemic composition for reducing chronoageing and/or photoageing of the skin preferably comprises the LXR activator, the retinoic acid and/or metabolic precursor and a physiologically acceptable vehicle.

Topical Formulations

A topical composition according to the invention will usually contain a dermatologically acceptable vehicle. A dermatologically acceptable vehicle acts as a dilutant, dispersant or carrier for the LXR activator(s) and retinoic acid and/or metabolic precursor(s) in the composition, so as to facilitate its distribution when the composition is topically applied.

Dermatologically acceptable vehicles other than water can include liquid or solid emollients, solvents, humectants, thickeners and powders. Examples of each of these types of vehicle which can be used singly or as mixtures of one or more vehicles, are as follows:

Emollients, such as stearyl alcohol, glycerol monoricinoleate, glycerol monostearate, mink oil, cetyl alcohol, isopropyl isostearate, stearic acid, isobutyl palmitate, isocetyl stearate, oleyl alcohol, isopropyl luarate, hexyl laurate, decyl oleate, octadecan-2-ol, isocetyl alcohol, eicosanylalcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, palm kernal oil, rapeseed oil, safflower seed oil, evening primrose oil, soybean oil, sunflower seed oil, avocado oil, olive oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate;

Propellants such as trichlorofluoromethane, dichlorodifluoro-methane, dichlorotetrafluoroethane, monochlorodifluoromethane, trichlorotrifluoroethane, propane, butane isobutanem demethyl ether, carbon dioxide, nitrous oxide;

Solvents such as ethyl alcohol, methylene chloride, isopropanol, acetone, ethylene glycol monoethyl ether, diethylene glycol monobutyl ether, diethylene glycol monoethyl ether, dimethyl sulphoxide, dimethyl formamide, tetrahydrofuran;

Powders, such as chalk, talc, fullers earth, kaolin, starch, gums, colloidal silica sodium polacrylate, tetre alkyl and/or trialkyl aryl ammonium smectites, chemically modified magnesium aluminium silicate, organically modified montmorillonite clay, hydrated aluminium silicate, fumed silica, carboxyvinyl polmer, sodium carboxymethyl cellulose, ethylene glycol monostearate.

The dermatologically acceptable vehicle will usually form from 10 to 99.99 wt %, preferably from 50 to 99 wt % of the final composition ready for use by the consumer.

The composition may also comprise water, usually up to 98% volume, preferably 5 to 80% volume of said final composition.

One class of embodiments comprises a cosmetic method of providing at least one skin care benefit selected from preventing or reducing wrinkles, fine lines, sagging, loss of elasticity, loss of firmness, dermal and/or epidermal thinning, age spots and loss of "shine/vitality/glow/radiance", the method comprising applying to the skin, a topical composition of the invention as described above.

A topical or skin composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas or above at a temperature of 20° C. The composition may be packaged in a container to suit its viscosity and intended use by the consumer. For example a lotion or fluid cream can be packaged in a bottle or a roll-ball applicator or a propellant driven aerosol device or a container fitted with a pump suitable for finger operation. When the composition is a cream, it can simply be stored in a non-deformable bottle or a squeeze container, such as a tub or a lidded jar.

As already mentioned, compositions of the invention for topical application include personal wash compositions such as liquid soaps, solid soaps, gels, and oils for washing in either the bath or in a shower or for use as a skin moisturising or conditioning product in shower or bath.

The present invention relates to cosmetic methods of methods of reducing chronoageing and/or photoageing of the skin. The present invention also relates to methods of enhancing the effect of retinoic acid on skin cells. In one embodiment, such methods comprise the administration of a safe and effective amount of a composition of the invention to the skin or regions thereof. The amount of active agent and frequency of application will vary depending on the initial condition of the skin and the desired end result.

A safe and effective amount of active in a topical composition is applied, generally from about 1 μg to about 1 mg per $cm^2$ skin per application, preferably from about 2 μg to about 800 μg/$cm^2$ skin per application, more preferably from about 30 μg to about 700 μg/$cm^2$ skin, most preferably from about 75 μg to about 250 μg/$cm^2$ skin. Frequency of application typically ranges from about four times a day to about twice a week, more preferably from about three times a day to about once every other day, more preferably at least twice daily. It is generally preferred that at least one application occurs in the evening.

Systemic Formulations

A composition according to the present invention for systemic administration may for example be adapted for oral administration, e.g. in the form of a tablet, lozenge, capsule, liquid (e.g. syrup or linctus) or as an injection (e.g. subcutaneous or intramuscular) or infusion or as a suppository. Typical such formulation techniques and appropriate pharmacologically acceptable carriers are well known to those skilled in the art. Suitable compositions for oral administration include those adapted for delayed release and/or for release in the lower gastrointestinal tract.

The amount of the active ingredients administered depends upon the bioavailability of the compound from the composition, in particular where oral administration is used. Typically, however, the LXR activating agents and the retinoic acid or precursor thereto are each dosed in an amount of from about 0.01 mg/kg of body weight to about 100 mg/kg, preferably from about 0.1 to about 30 mg/kg of body weight. The amount of the composition depends upon the percent of compound within its formula, which is a function of the amount of the compound required per dose, its stability, release characteristics and other pharmaceutical parameters. The doses are typically administered from once or twice weekly to one or twice daily.

The routes of administration and dosages described are intended only as a guide since a skilled practitioner will be able to determine readily the optimum route of administration and dosage for any particular individual.

Another means of systemic dosing comprises dosing any of the aforementioned compositions in a food product which therefore does not necessarily require use of a pharmacologically/pharmaceutically acceptable carrier.

As used herein, the term "food products" includes both food products as such and beverages. Suitable food products as such include spreads, dairy products (including milk and yoghurts), desserts, convenience foods/snacks, breakfast cereals and cereal bars, ready-cook meals, bread and frozen confections such as ice creams, water ices and sorbets and yoghurt ice creams. Food products also include dietary/nutritional supplements. Suitable beverages include tea, tea-flavoured drinks, coffee, soft drinks (e.g. carbonated squashes etc) and fruit juice.

The food products are typically supplemented with the active ingredients of the invention so that they contain higher amounts of the active ingredient(s) than they would normally contain.

Another class of embodiments comprises a method of providing at least one skin care benefit selected from preventing or reducing wrinkles, fine lines, sagging, loss of elasticity, loss of firmness, dermal and/or epidermal thinning, age spots and loss of "shine/vitality/glow/radiance", the method comprising administering orally, a systemic composition of the invention as described above, or a food product of the invention as described above. The present invention also relates to methods of enhancing the effect of retinoic acid on skin cells by administering systemically, such as orally, a systemic composition of the invention as described above, or a food product of the invention as described above.

The invention also provides a closed container containing a cosmetically acceptable composition as herein defined.

The present invention will now be described further with reference to the following examples which are illustrative only and non-limiting.

Example 1

This is an evaluation of the ability of LXR activators to enhance the effect of retinoic acid on retinoic acid mediated gene expression, (i) using a reporter gene assay and (ii) measuring levels of expression of CRABPII in fibroblast cells. This is a predictor of effects on reducing chronoageing and/or photoageing because the activity of the genes tested is associated with reversing the physiological changes induced by chronological ageing and/or photoageing.

Reporter Gene Assay

The assay was performed by transient transfection of Cos-7 cells with a mixture of five DNA plasmids. These are 1) RAR reporter gene construct (Gift from David Talmage, Columbia University, USA). Modified pCAT-promoter reporter vector (Chloramphenicol acetyltransferase reporter vector commercially available form Promega). Containing a tandem repeat of 5 RAR response elements (RAREs) corresponding to the RARE found in the mouse RARbeta gene promoter region. 2) Over-expressing RARγ construct (Gift from Thomas Perlmann, Karolinska Institute, Sweden). Modified pCMX vector containing the coding region of a human RARγ cDNA inserted downstream of the CMV promoter. 3) Over-expressing RXRα construct (Gift of V. K. K. Chatterjee, Addenbrooke's Hospital, Cambridge). Modified pRSVcat containing the coding region of a human RXRα cDNA downstream of the RSV promoter. 4) Over-expressing LXRα construct commercially available from Invitrogen (GeneStorm hORF Expression Vector Accession no. U22662) Modified pcDNA3.1/GS containing the coding region of human LXRα. 5) Control luciferase construct (pRL-TK Renilla luciferase reporter vector commercially available from Promega. For the transfection, DNA was made up as a mix of RARE reporter gene:RARγ:RXRα:LXRα: pRLTK in the ratio 4.15:4.95:3.33:8.97:1.

Cos-7 cells were grown in DMEM with 10% FCS (foetal calf serum) at 37° C., 5% $CO_2$ to 80% confluency. Cells were then plated out in 24 well plates at 50,000 cells per well and incubated overnight in DMEM with 10% FCS at 37° C., 5% $CO_2$. Cells were then transfected using the LipofectAMINE reagent (GibcoBRL). For each well 0.5 μg of DNA mix (in 25 μl of DMEM) was incubated with 1.1 μl LipofectAMINE (in 25 μl of DMEM) for 45 minutes. The mixture was then made up to 250 μl per well and added to the cells, which had been washed with 1 ml of DMEM. Cells were then incubated for 5 hours at 37° C., 5% $CO_2$ and 250 μl DMEM with 20% SBCS (charcoal stripped bovine calf serum) added. Cells were incubated for 18 hours at 37° C., 5% $CO_2$ before being treated with the appropriate compound/extract. Test compounds were made up as 1000× stocks (in DMSO or ethanol as appropriate) and diluted into DMEM with 10% SBCS (500 □l per well) immediately before being added to cells. Each treatment was performed in triplicate. The transfection mix was removed from the cells and replaced with the treatment mix, and incubated for 24 hours at 37° C., 5% $CO_2$. Cells were washed with 1 ml of PBS (without calcium or magnesium) and then lysed with 100 μl per well of 1× Lysis Buffer (as supplied with Promega Renilla Luciferase assay kit). Lysis was allowed to continue for 15 minutes and then the lysate was assayed for Renilla luciferase activity using the Promega Renilla Luciferase assay kit. For the assay 20 μl of lysate was taken and assayed as described in the kit instructions using a MLX microtiter plate luminometer (Dynex). 75 μl of lysate was assayed for chlorampenicol acetyltransferase activity using the Roche CAT ELISA kit as per the manufacturer's instructions.

CAT activity (RAR driven) was normalised against the Renilla luciferase value for that well and the mean calculated for the three wells treated with the same agent. Activity was then expressed as fold activation over the vehicle (ethanol) control values for that particular plate.

TABLE 1

| Treatment | Fold activity +/− sd (n = 3) |
|---|---|
| Ethanol | 1.000 +/− 0.164 |
| 0.1 μM all-trans retinoic acid | 1.733 +/− 0.445 |
| 35 μM 22R hydroxycholesterol | 1.209 +/− 0.030 |
| 0.1 μM all-trans retinoic acid and 35 μM 22R hydroxycholesterol | 2.962 +/− 0.582 |

Fibroblast Expression of CRABPII.

Primary dermal fibroblasts were cultured in DMEM with 10% FCS (foetal calf serum) at 37° C., 5% $CO_2$, 20% $O_2$ to 80% confluency. Cells were then plated out in 12 well plates at 38,000 cells per well, and incubated for 24 hours. Medium was replaced and cells incubated for a further 24 hours at 37° C., 5% $CO_2$, 4% $O_2$. Cells were treated with vehicle (ethanol) or 22R hydroxycholesterol and/or retinoic acid in 1 ml fresh medium (DMEM plus 10% FCS). Treatments were prepared as fresh 1000× stocks and diluted into medium immediately before addition to the cells. Treatment was for 24 hours at 37° C., 5% $CO_2$, 20% $O_2$. Cells were washed in 1 ml phosphate buffer saline and trypsinised from the plates. Cells were pelleted at 13000 g for 5 min and washed with 1 ml PBS. Cells were re-pelleted and re-suspended in protein lysis buffer (4M urea, 0.5% SDS, 10 mM EDTA in PBS with protease inhibitor cocktail). Samples were equilibrated for total protein content and the proteins separated by SDS-PAGE and blotted to nitrocellulose. Membranes were probed with antisera against the CRABPII protein and detected by ECL-plus. Intensity of signal was captured using a STORM scanner and quantified using ImageQuant 5.2.

TABLE 2

| Treatment | Band Intensity (arbitrary units) | Relative band intensity | % change from vehicle |
|---|---|---|---|
| Vehicle | 168984.95 | 1.000 | 0 |
| 1 nM all-trans retinoic acid | 228603.88 | 1.353 | +35.3% |
| 5 μM 22R-hydroxycholesterol | 167664.2 | 0.992 | −0.8% |
| 1 nM all-trans retinoic acid and 5 μM 22R-hydroxycholesterol | 272710.54 | 1.614 | +61.4% |

The various features and embodiments of the present invention, referred to in individual sections above apply, as appropriate, to other sections, mutatis mutandis. Consequently features specified in one section may be combined with features specified in other sections, as appropriate.

All publications mentioned in the above specification are herein incorporated by reference. Various modifications and variations of the described methods and products of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in the relevant fields are intended to be within the scope of the following claims.

The invention claimed is:

1. A method for reducing chronoageing and/or photoageing of the skin by providing at least one skin care benefit selected from reducing wrinkles, fine lines, sagging, loss of elasticity, loss of firmness, dermal thinning, epidermal thinning and age spots; said method comprising administering to an individual a composition comprising (i) an LXR activator other than 25-hydroxycholesterol and (ii) a retinoid selected from retinyl esters of all-trans rentinol, all-trans retinol, all-trans retinal, all-trans retinoic acid and mixtures thereof; wherein the LXR activator comprises a compound of formula (B):

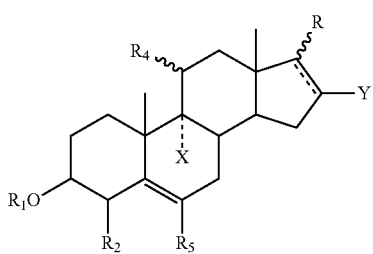

wherein;
R is a $C_1$ to $C_{10}$ unsubstituted, branched and unsaturated alkyl group, and wherein $R_1$; $R_2$, $R_4$, $R_5$, X, and Y are all hydrogen,
wherein the mixture of LXR activator and retinoic acid act synergistically to upregulate CRAB P II expression when tested in vitro in dermal fibroblasts, and wherein the composition is either a topical composition comprising from 0.01% to 10% by weight of the LXR activator and from 0.001 to 10% by weight of the retinoid, the balance comprising at least one dermatologically acceptable carrier; or the composition is a systemic composition comprising from 0.01% to 10% by weight of the LXR activator and from 0.001 to 10% by weight of the retinoid, the balance comprising at least one pharmaceutically acceptable carrier.

2. The method according to claim 1 wherein the LXR activator is provided in the form of one or more extracts of natural plant sources.

3. The method according to claim 2 wherein the natural plant sources is selected from the group consisting of more of *Commiphora mokul, Boswelta serrata*, Dragon's blood resin, apple peel, allspice, clove, Damar gum, Nettle, red seaweed, Breuzihno resin, mastic gum, mountain ash berry and plantain.

4. The method according to claim 1 wherein the composition is administered to the individual by topical application to the skin.

* * * * *